US008876020B2

(12) United States Patent
Holladay et al.

(10) Patent No.: US 8,876,020 B2
(45) Date of Patent: Nov. 4, 2014

(54) SPRAYABLE GEL WOUND DRESSING

(75) Inventors: Robert J. Holladay, Saratoga, UT (US);
Nathan R. Moeller, Highland, UT (US);
William D. Moeller, Alpine, UT (US)

(73) Assignee: American Silver LLC, Alpine, UT (US)

( * ) Notice: Subject to any disclaimer, the term of this patent is extended or adjusted under 35 U.S.C. 154(b) by 214 days.

(21) Appl. No.: 13/115,926

(22) Filed: May 25, 2011

(65) Prior Publication Data

US 2012/0298777 A1     Nov. 29, 2012

(51) Int. Cl.
*B01D 17/00*     (2006.01)
*A61L 26/00*     (2006.01)

(52) U.S. Cl.
CPC ......... *A61L 26/0014* (2013.01); *A61L 26/0076* (2013.01); *A61L 26/008* (2013.01); *A61L 2300/104* (2013.01); *A61L 26/0066* (2013.01); *A61L 2300/404* (2013.01)
USPC .......................................... 239/328; 239/327

(58) Field of Classification Search
CPC ............. B05D 7/2481; B05D 11/0016; B05D 11/0337
USPC ......... 239/327, 328, 329, 330, 356, 362, 363; 222/95, 105, 386.5
See application file for complete search history.

(56) References Cited

U.S. PATENT DOCUMENTS

| 2,008,131 | A | * | 7/1935 | Wilhelm et al. | 424/443 |
| 3,257,036 | A | * | 6/1966 | Micallef | 222/95 |
| 3,788,521 | A | * | 1/1974 | Laauwe | 222/94 |
| 3,938,708 | A | * | 2/1976 | Burger | 222/95 |
| 7,793,735 | B2 | * | 9/2010 | Hagar | 169/46 |
| 2005/0266081 | A1 | * | 12/2005 | Rogozinski | 424/484 |
| 2009/0226541 | A1 | * | 9/2009 | Scholz et al. | 424/672 |

* cited by examiner

*Primary Examiner* — Davis Hwu
(74) *Attorney, Agent, or Firm* — Stefan J. Kirchanski; Venable LLP

(57) ABSTRACT

A sprayable hydrogel wound dressing composed of an aqueous solution of neutralized Carbopol and silver hydrosol of silver nanoparticles electrolytically formed from silver metal without the use or inclusion of organic materials. The hydrogel is sprayed with a physical barrier sprayer system which separates the hydrogel from the propellant. The hydrogel is thixotropic/shear thinning so that the viscosity of the hydrogel is sufficient reduced in the sprayer to allow spray formation and regains sufficient viscosity to resist running when deposited on a vertical surface.

4 Claims, No Drawings

SPRAYABLE GEL WOUND DRESSING

CROSS-REFERENCE TO PRIOR APPLICATIONS

Not Applicable

U.S. GOVERNMENT SUPPORT

Not Applicable

AREA OF THE ART

The present invention is in the area of hydrogel compositions for use as wound dressing and more particularly concerns a sprayable silver hydrosol hydrogel composition.

DESCRIPTION OF THE INVENTION

There is a continuing need for effective wound dressing materials. By "wound" in this instance is meant any type of damage to the external surface of the human body. Most usually this means damage to the skin (epidermal) surface but can also include damage to mucosal surfaces found in body orifices (such as the mouth) opening onto the skin surface. The damage involved can be of any type such as a cut, tear, contusion, scrape, scratch or burn. That is, any physical damage to the integrity of the epidermis.

Traditionally, a dressing included any type of bandage or cloth that protected the wound and in the case of deep wounds held the wound closed to prevent bleeding. A basic function of a dressing is to protect wounds from infection and other adverse environmental factors while promoting—or at least not inhibiting—healing. The traditional bandage cushions the wound from damaging contacts and absorbs wound exudate if present. Today, wound dressings also include a wide variety of topically applied liquids and semi-solids (ointments, creams, gels and the like) that protect the wound and promote healing. Because these types of materials generally don't provide the physical barrier protection of a bandage, they are usually used in conjunction with a more traditional fabric bandage. The topically applied liquids/semi-solids do, however, promote sterility, prevent desiccation and may include additives to suppress pain and/or promote healing.

Gel dressings, particularly hydrogel dressings, have proven to be extremely successful wound dressings because they provide barrier properties and are unusually compatible with damaged tissue. A gel is essentially a combination between a liquid phase and a solid phase in which the solid phase is in the form of a microscopic network that entraps regions of liquid phase. This results in a semi-solid material that is deformable and generally shows some properties of flow. In a hydrogel the insoluble solid is hydrophilic while the liquid is aqueous—either pure water or a water solution. Because a hydrogel contains water as its major ingredient, the dressing prevents desiccation of delicate tissues. Many hydrogels can also absorb an additional quantity of water; thus, they can also tolerate wound exudate without being washed away. In addition, the aqueous phase can contain a variety of active ingredients including germicidal agents and hormones/growth factors that promote healing Moreover, most hydrogels are generally ultimately water soluble or miscible with water which allows one to easily wash away the hydrogel when replacement of the dressing becomes necessary.

Depending on the ratio of hydrophilic solid to aqueous solutions hydrogels can range from being quite firm (even to the point that they can be attached to a wound using adhesive strips and the like) to being quite soft generally having a viscosity similar to a typical topical cream or ointment. It will be appreciated that management of delicate wounds (particularly burns) may demand the use of a very soft hydrogel because of the likelihood of a more firm hydrogel causing mechanical damage to the wound during application or removal. In addition, difficult to heal wounds such as skin ulcers may not be suited to a firm gel because such a gel is unable contact the wounded tissue within the ulcer to promote healing. However, there is a possible dilemma in the choice of firm versus soft gel. While the firm hydrogel is more likely to cause mechanical damage if it rubs delicate tissue, it is relatively simple to take a sterile firm hydrogel from a sterile package and apply it to a wound surface without introducing any microbial contamination. A soft hydrogel, however, must be spread over the wound generally using some type of applicator. The use of an applicator significantly increases the possibility that microbial contaminants will be introduced. In addition, where the wound surface is particularly delicate, the act of spreading the hydrogel with an applicator may itself result in mechanical damage.

In the case of extremely fragile wounds such as serious burns, spraying liquid treatments on to the wound has long been favored. Because such wounds are extremely prone to infection, antibiotics or anti-germicides are often sprayed on burns. With a spray no physical applicator is used, thereby avoiding the danger of wound trauma or contamination. Following the spraying the burn is protected with a light gauze or similar dressing. The problem with such a spray is that it does not usually provide much in the way of an anti-desiccation barrier. One solution to this problem is disclosed by U.S. Pat. No. 3,987,000 to Gleichenhagen et al. which shows a sprayable polymer composition. The composition may be sprayed or thinly coated onto an open wound. The disclosed composition is a binary system that sprays a powder and a solvent to form a film on the wound in situ. The insoluble film that is formed can be semipermeable and hydrophilic. This provides the ease and safety of a spray application and yet provides an anti-desiccation barrier. Unfortunately, it is difficult to remove the insoluble film without damaging the wound. If the wound is not too serious, the film merely sloughs off as healing progresses. However, if the wound needs to be cleaned and medication reapplied, such an insoluble film can pose a problem.

All in all what is really needed is the ability to spray a semi-firm hydrogel onto a wound. The problem faced by the art is that a hydrogel that is sufficiently firm to stay in place on a wound surface (i.e., does not run, puddle or get absorbed by any covering bandage material) is too thick to be sprayed effectively. The most common attempted solution has taken a clue from Gleichenhagen et al.—namely, multiple components are sprayed to form a gel in situ. For example, U.S. Pat. No. 6,179,862 to Sawhney discloses a "binary" system in which a gel is actually formed on the wound through the mixing of two separate components. U.S. Patent Application Publication Number 2002/0122771 (Holland et al.) shows a wound dressing that is formed on the wound by the spray application of a composition which gels in situ to form a hydrogel. However, reagents and apparatus necessary for binary sprays and in situ gelling agents may either be overly expensive and/or may not be the optimal formulations for wound protection and healing. In addition, there are gels that are applied with a "trigger spray" which is a mechanical pump much like the ones used to spray on window cleaner. The problem with these products has been that the inherent viscosity of the gel causes the spray to be relatively coarse—even stream-like. Not the ideal way of evenly applying hydrogels to delicate tissues.

Nevertheless, a sprayable gel dressing that can be applied as a mist or spray of small droplets has a number of advantages. As already alluded to, spray application prevents contamination of the wound because no potentially contaminated applicator is involved. If the gel is sterile and the applicator nozzle is protected from touching a contaminated surface (e.g., fingers), the applied gel will be sterile. The advantage of not using a physical applicator also works in the other direction. If an applicator is used to apply the gel, the applicator may become contaminated by bacteria growing in the wound. This presents a very real danger of these bacteria colonizing the health care professional or otherwise becoming spread about the facility and spread to other patients. Since a spray applicator nozzle never comes in contact with any contaminant, there is no danger of spreading infection. Nor is it necessary to laboriously disinfect the nozzle between uses. Because a physical applicator such as a spatula is not involved there is no danger of causing pain to the patient during the application of the spray nor is there any likelihood of causing mechanical damage to the wound. If the spray droplets are relatively fine (as opposed to coarse droplets or a stream), application is even and the wound is not disturbed. Furthermore, spray application is more even (areas are not missed) and the spray is often able to reach areas (e.g., within a skin ulcer) that cannot be readily reached with typical applicators. Also, an effective sprayable hydrogel can be sprayed into incisions prior to and during closure—something that cannot be readily achieved with typical applicators such as spatulas. Plus, a properly designed spray system allows one-handed application of the gel.

After investigating this problem the inventors determined that a pressurized spray system was preferable to a mechanically pumped system. A pressurized system allows easy and reproducible one-handed application. Having to squeeze a pump handle often causes the aim of the spray to wander. Also, there is a tendency to produce uneven and excessively coarse sprays with a mechanical pump. On the other hand, the typical propellant driven (AKA "aerosol") spray system is not suitable for a gel product. Such devices operate by having a liquid propellant which boils at a temperature near to room temperature evenly mixed with the material to be sprayed (Generally the propellant and the sprayable material must be miscible). When the sprayer valve is opened, pressure in the container drops allowing the propellant liquid to boil, thereby forcing the propellant/sprayable material mixture up a dip tube and out through a nozzle. At atmospheric pressure the liquid propellant rapidly vaporizes leaving a stream of fine particles of sprayable material embedded in a stream of gas. Hydrogel compositions are generally not miscible with propellants (many of which are hydrophobic) and are often too viscous to be forced up the tube into the nozzle. Not only are there compatibility/miscibility problems between the propellant and the sprayable mixture, but the propellant itself may not be ideally suited for contact with delicate wounded tissue.

The present inventors realized that an ideal solution to the problem of providing a spray hydrogel wound treatment would be the use of pressurized sprayers in which the propellant and the sprayable material are kept separate by a physical barrier. In one embodiment of such sprayers, the sprayable material is enclosed by a flexible membrane (e.g., a mylar bag—so-called Bag-On-Valve (BOV) sprayer) to separate the propellant from the sprayable material. With the BOV sprayer the bag enclosed sprayable material is suspended within a structure (e.g., a can) and surrounded by propellant (usually pressurized gas). The propellant is at a pressure significantly above atmospheric pressure. The sprayer nozzle is connected by means of a valve to the enclosed sprayable material. When the valve is operated, the sprayable material is squeezed out of the flexible membrane enclosure and through the nozzle to be emitted as a spray of fine droplets. Because the material is directly forced into the nozzle without being mixed with the propellant, the system can work with materials such as hydrogels that are not miscible with propellants. Because the energy for achieving a spray is supplied by the propellant, a user can readily and evenly apply the spray with a single hand. Similar results can be obtained with other barrier sprayers such as a so-called "piston" system where a sliding diaphragm separates the propellant from the sprayable material.

BOV dispensers have long been used to dispense gels such as shaving gels, but until now they have not been used to spray hydrogels. This is because the typical hydrogel is still too viscous to be forced into a spray mist (at least by the pressures safely attainable). However, reducing a hydrogel's viscosity to that of a readily sprayable liquid results in a gel that readily runs after application. The present inventors realized that certain hydrogels demonstrate atypical viscosity properties—namely the gels show either thixotropy or shear thinning. A thixotropic gel will show a decrease in viscosity over time at a constant shear stress while a shear thinning gel will display decreasing viscosity with increasing shear rate. The precise distinction is not important to the present application. The point is that when a gel showing either or both of these properties is forced through a nozzle, its viscosity is reduced and may attain a sufficiently low viscosity to allow spray droplets to form readily. Then after the droplets come to rest, the process reverses and the hydrogel regains its initial level of viscosity. Thus, the solution to the sprayability problem is select a thixotropic/shear thinning hydrogel and reduce its inherent viscosity sufficiently to allow it to be sprayed but leave the viscosity sufficiently high that the sprayed gel resists running when it regains its initial viscosity after being sprayed. This approach is not effective with a non-thixotropic/shear thinning hydrogel because when the viscosity of the gel is sufficiently reduce to permit effective spraying, the resulting sprayed material is too thin and runs and/or is rapidly absorbed by bandage materials.

For any particular hydrogel formulation it is possible to test the hydrogel in a BOV sprayer or other barrier sprayer. In the sprayer the inside of the flexible bag is connected to the outside of the sprayer by a passageway controlled by a valve. When the valve is opened, the greater pressure within the sprayer container forces the content of the flexible bag through the valve and then out through the nozzle's aperture into the outside air as a fine spray. If the contents of the flexible bag are excessively viscous they will either be too thick to flow through the passageway and aperture or will flow too slowly to permit dispersion into a spray. If a non-thixotropic/non-shear thinning gel is used in such a sprayer, it is possible to reduce the viscosity of the gel until the viscosity is low enough to permit spray formation. In such a case, however, the sprayed material will be overly thin and will run or sag. If a thixotropic/shear thinning gel is tested, it is possible to successively reduce the viscosity of the gel until it is just thin enough to flow through the passageway and form a spray. Because the viscosity is temporarily reduced as the gel is forced through the passageway and the aperture, the sprayed material will regain viscosity and will resist running and sagging.

The inventors have found that a hydrogel made by dissolving Carbopol ETD 2020 (cross-linked acrylic acid copolymer manufactured by the Lubrizol Corporation of Wickliffe, Ohio) in ASAP 32 ppm proprietary nanosilver particle solution (hydrosol) (manufactured by American Biotech Labs, LLC of Alpine, Utah) and neutralizing the mixture with triethanolamine is an extremely effective antibacterial hydrogel. As illustrated in Table 1 a typical formulation contains 91% silver hydrosol (about 30 ppm silver final concentration), 7.0% propylene glycol and 0.58% (by weight) Carbopol ETD 2020. When this mixture is neutralized with 1% triethanolamine it has a viscosity between 50,000 and 70,000 cP as measured with a Brookfield viscometer. It was discovered that reducing both the Carbopol and the triethanolamine concentrations is a simple and reliable way to reduce the viscosity of the hydrogel. If the viscosity of the gel is reduced to the 16,000-20,000 cP range, it can be dispensed with a pump spray gel bottle. However, if the viscosity of the gel is reduced to the 8,000-10,000 cP range it can be readily sprayed by a pressurized BOV sprayer. In that case the gel is dispensed as an even spray of fine droplets which is capable of depositing a layer approximately ⅛ of an inch thick on a vertical skin surface. If excessive gel is deposited, the layer may sag and run but a layer at least 1/16 of an inch remains. Thus, by reducing the initial viscosity of a thixotropic/shear thinning hydrogel one can produce a sprayable hydrogel that deposits an even and thick layer that resists running or sagging.

TABLE 1

| Components | Typical Wound Gel | Sprayable Wound Gel |
| --- | --- | --- |
| ASAP Solution, 32 ppm silver | 91% | 91% |
| Propylene Glycol | 7.0% | 7.0% |
| Triethanolamine | 1.0% | 0.105% |
| Carbopol ETD 2020 | 0.58% | 0.061% |
| Distilled water | Remainder | Remainder |
| Viscosity | 50,000-70,000 cP (Brookfield) | 8,000-10,000 cP (Brookfield) |

One of ordinary skill in the art will recognize that the formula given above is merely illustrative of one type of thixotropic/shear thinning hydrogel. The art of hydrogels recognizes that a large number of hydrophilic polymers (including botanical gums, agar products and carrageenan) can be used to produce hydrogels that show thixotropic/shear thinning properties. Different types and combinations of hydrophilic polymers show differing degrees of thixotropy. It is necessary to adjust the initial viscosity of the material to obtain optimal sprayable hydrogel. Different gel combinations have different optimum sprayable viscosities. Where a given hydrogel shows greater thixotropic/shear thinning properties than the Carbopol example, a viscosity higher than 8,000-10,000 cP might be useable. The advantage of such a combination can be that the sprayed gel will have higher viscosity and accumulate to even greater thicknesses than the sprayed Carbopol-based gel.

However, the inventors and their colleagues already have produced considerable experimental data verifying the antimicrobial properties and the healing promoting properties of a Carbopol-based hydrogel that contained the particular nanoparticle silver composition manufactured by American Biotech Labs, LLC. When a sprayable form of the same gel (i.e., same gelling agent and same concentration of proprietary silver hydrosol) is produced, all of the antimicrobial data are directly applicable to the sprayable gel. Therefore, the contents of PCT/US2004/017567 and PCT/US2005/047699 which show results for a non-sprayable Carbopol-based silver containing gel are incorporated herein by reference. Those references show that silver concentrations down to about 1 ppm are effective. As might be expected higher silver concentrations of 20 and 32 ppm are even more effective against certain organisms. The present inventors have also demonstrated that silver concentrations up to about 200 ppm are usable in the present invention. One of ordinary skill in the art will recognize that reducing the viscosity of the hydrogel would not be expected to alter any of the reported results. This same method can be advantageously applied to another thixotropic/shear thinning hydrogel that shows greater thixotropic properties than Carbopol-based gels.

The following claims are thus to be understood to include what is specifically illustrated and described above, what is conceptually equivalent, what can be obviously substituted and also what essentially incorporates the essential idea of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A nanoparticle silver hydrogel sprayer system comprising:
   a pressurized bag on valve sprayer comprising a pressurized container, a flexible bag within the pressurized container, and a valve operable to connect an inlet inside of the flexible bag with an outlet outside of the pressurized container;
   an aqueous thixotropic/shear thinning hydrogel having an initial viscosity of about 8,000 to 10,000 cP and containing between 1-200 ppm total silver in the form of metallic silver nanoparticles wherein said silver nanoparticles have a surface of silver oxide and wherein said silver nanoparticles are produced electrolytically from silver metal without using any organic material, said hydrogel disposed inside of the flexible bag without propellant; and
   a nozzle in fluidic communication with the outlet so that operation of the valve allows said hydrogel to be forced through the valve where shear forces temporarily reduce said hydrogel's viscosity from the initial viscosity thereby allowing said hydrogel to be dispersed by the nozzle as a mist or spray of fine droplets which then deposits on a surface to form a layer of hydrogel having a final viscosity about equal to the initial viscosity, said layer resistant to running or sagging.

2. The nanoparticle silver hydrogel sprayer system according to claim 1, wherein the hydrogel comprises an aqueous solution of neutralized Carbopol.

3. A nanoparticle silver hydrogel sprayer system comprising:
   a pressurized bag on valve sprayer comprising a pressurized container, a flexible bag within the pressurized container, and a valve operable to connect an inlet inside of the flexible bag with an outlet outside of the pressurized container;
   an aqueous thixotropic/shear thinning hydrogel comprising neutralized Carbopol solution having an initial viscosity of about 8,000 to 10,000 cP and containing between 1-200 ppm total silver in the form of metallic silver nanoparticles wherein said silver nanoparticles have a surface of silver oxide and wherein said silver nanoparticles are produced electrolytically from silver metal without using any organic material, said hydrogel disposed inside of the flexible bag without propellant; and
   a nozzle in fluidic communication with the outlet so that operation of the valve allows said hydrogel to be forced through the valve thereby where shear forces temporarily reduce said hydrogel's viscosity from the initial viscosity thereby allowing said hydrogel to be dispersed by the nozzle as a mist or spray of fine droplets which then deposits on a surface to form a layer of hydrogel having a final viscosity about equal to the initial viscosity, said layer resistant to running or sagging.

4. A method for furnishing a sprayable hydrogel comprising the steps of:

providing a pressurized sprayer wherein a propellant is physically separated from a sprayable material by a barrier;

selecting a thixotropic/shear thinning aqueous hydrogel of Carbopol having a viscosity between about 8,000 and 10,000 cP;

loading the thixotropic/shear thinning aqueous hydrogel into the pressurized sprayer as the sprayable material; and operating the pressurized sprayer, the viscosity of the sprayable material being sufficiently low so as to enter into a spray nozzle of the pressurized sprayer where the viscosity is further reduced thereby generating a mist or spray of fine droplets which can deposit in a layer at least ⅛ inch thick when sprayed on a vertical surface.

* * * * *